US010352159B2

(12) United States Patent
Rowe (10) Patent No.: US 10,352,159 B2
(45) Date of Patent: Jul. 16, 2019

(54) MONITORING OF DRILLING OPERATIONS USING DISCRETIZED FLUID FLOWS (71) Applicant: Halliburton Energy Services, Inc., Houston, TX (US)

(72) Inventor: Mathew Dennis Rowe, Lafayette, LA (US)

(73) Assignee: Halliburton Energy Services, Inc., Houston, TX (US)

(*) Notice: Subject to any disclaimer, the term of this patent is extended or adjusted under 35 U.S.C. 154(b) by 325 days.

(21) Appl. No.: 15/301,988

(22) PCT Filed: May 15, 2014

(86) PCT No.: PCT/US2014/038223
§ 371 (c)(1),
(2) Date: Oct. 5, 2016

(87) PCT Pub. No.: WO2015/174991
PCT Pub. Date: Nov. 19, 2015

(65) Prior Publication Data
US 2017/0145822 A1 May 25, 2017

(51) Int. Cl.
*E21B 49/08* (2006.01)
*E21B 21/08* (2006.01)
(Continued)

(52) U.S. Cl.
CPC ............. *E21B 49/08* (2013.01); *E21B 21/01* (2013.01); *E21B 21/065* (2013.01); *E21B 21/08* (2013.01);
(Continued)

(58) Field of Classification Search
CPC ........ E21B 49/003; E21B 49/08; E21B 21/01; E21B 21/065; E21B 44/00; E21B 21/08; E21B 202/007
See application file for complete search history.

(56) References Cited

U.S. PATENT DOCUMENTS 2,289,687 A * 7/1942 Stuart ................... E21B 49/005
                                                        204/408
2,930,967 A * 3/1960 Laird ...................... E21B 21/08
                                                        204/411
(Continued)

FOREIGN PATENT DOCUMENTS

DE          60111781 T2      5/2006
EP           2592222 A2      5/2013
(Continued)

OTHER PUBLICATIONS

International Preliminary Report on Patentability issued in related Application No. PCT/US2014/038223, dated Nov. 24, 2016 (6 pages).
(Continued)

*Primary Examiner* — Blake E Michener
(74) *Attorney, Agent, or Firm* — Jason Sedano; Baker Botts L.L.P.

(57) ABSTRACT

A system and method for monitoring drilling operations by dividing a flow of fluid into at least one discrete fluid unit, circulating the fluid unit through a wellbore, and comparing a measured change to a property of the fluid unit to a predicted change in the property of the fluid unit. In addition to measuring the change to the property of the fluid unit, the fluid unit may be tracked by iteratively calculating the location of the fluid unit as it passes through the wellbore. Data collected for the fluid unit by a control system may be analyzed and used by the control system or an operator to diagnose problems or improve overall efficiency of drilling operations.

19 Claims, 3 Drawing Sheets (51) Int. Cl.

| | | |
|---|---|---|
| *E21B 44/00* | (2006.01) | |
| *E21B 21/01* | (2006.01) | |
| *E21B 21/06* | (2006.01) | |
| *G01F 1/84* | (2006.01) | |
| *G01N 33/28* | (2006.01) | |
| *G08B 21/18* | (2006.01) | |
| *E21B 49/00* | (2006.01) | |
| *E21B 21/00* | (2006.01) | |

(52) U.S. Cl.
CPC ............ *E21B 44/00* (2013.01); *E21B 49/003* (2013.01); *G01F 1/8409* (2013.01); *G01N 33/2823* (2013.01); *G08B 21/182* (2013.01); *E21B 2021/007* (2013.01)

(56) References Cited

U.S. PATENT DOCUMENTS

| | | | | |
|---|---|---|---|---|
| 3,831,082 | A * | 8/1974 | Mazzagatti | E21B 21/08 |
| | | | | 324/333 |
| 5,165,275 | A * | 11/1992 | Donovan | E21B 47/1015 |
| | | | | 250/254 |
| 6,410,862 | B1 | 6/2002 | Lecann | |
| 7,562,723 | B2 | 7/2009 | Reitsma | |
| 2002/0112888 | A1 | 8/2002 | Leuchtenberg | |
| 2003/0024737 | A1* | 2/2003 | Chang | E21B 21/08 |
| | | | | 175/25 |
| 2011/0087459 | A1 | 4/2011 | Lazovsky et al. | |
| 2011/0139464 | A1* | 6/2011 | Henderson | E21B 21/01 |
| | | | | 166/370 |
| 2011/0139506 | A1* | 6/2011 | Lovorn | E21B 21/08 |
| | | | | 175/25 |
| 2011/0214882 | A1* | 9/2011 | Santos | E21B 21/08 |
| | | | | 166/373 |
| 2012/0255777 | A1* | 10/2012 | Bernard | E21B 21/08 |
| | | | | 175/25 |
| 2012/0292109 | A1* | 11/2012 | Lovorn | E21B 21/08 |
| | | | | 175/25 |
| 2013/0032401 | A1* | 2/2013 | Edbury | E21B 7/06 |
| | | | | 175/24 |
| 2013/0112404 | A1* | 5/2013 | Lovorn | E21B 21/08 |
| | | | | 166/250.01 |
| 2014/0110169 | A1* | 4/2014 | Santos | E21B 47/10 |
| | | | | 175/25 |
| 2014/0291023 | A1* | 10/2014 | Edbury | E21B 44/00 |
| | | | | 175/24 |
| 2015/0260035 | A1* | 9/2015 | Rowe | E21B 49/00 |
| | | | | 250/254 |
| 2016/0024905 | A1* | 1/2016 | Johnson | E21B 44/00 |
| | | | | 700/283 |
| 2016/0123139 | A1* | 5/2016 | Jamison | E21B 49/087 |
| | | | | 166/250.01 |
| 2017/0350842 | A1* | 12/2017 | Mohr | E21B 49/08 |

FOREIGN PATENT DOCUMENTS

| | | |
|---|---|---|
| WO | 2002/050398 A1 | 6/2002 |
| WO | 2011/047236 A1 | 4/2011 |
| WO | 2012/016045 A1 | 2/2012 |
| WO | 2013/152073 A2 | 10/2013 |

OTHER PUBLICATIONS

Norman, J., Coriolis sensors open lines to real-time data, Drilling Contractor, http://www2.emersonprocess.com/siteadmincenter/PM%20Micro%20Motion%20Documents/Coriolis-Sensors-Real-Time-Data-AR-001462.pdf, 4 pages.

Mazerov, K., Automated control system integrates preventive and predictive maintenance funtions, Drilling Contractor, http://www.drillingcontractor.org/automated-control-system-integrates-preventive-and-predictive-maintenance-functions-23503, 2 pages.

International Search Report and Written Opinion issued in related PCT Application No. PCT/US2014/038223 dated Feb. 10, 2015.

* cited by examiner

MONITORING OF DRILLING OPERATIONS USING DISCRETIZED FLUID FLOWS

CROSS-REFERENCE TO RELATED APPLICATION

The present application is a U.S. National Stage Application of International Application No. PCT/US2014/038223 filed May 15, 2014, which is incorporated herein by reference in its entirety for all purposes.

TECHNICAL FIELD

The present invention relates to monitoring operations during drilling of subsurface formations, in particular subsurface formations containing hydrocarbon deposits.

BACKGROUND

During drilling of an oil or gas well, drilling fluids are circulated through the wellbore. The drilling fluids perform a variety of functions including cooling the drill bit, sweeping away cuttings from the bottom of the wellbore, and maintaining hydrostatic pressure to prevent blowouts or collapse of the wellbore.

As a drilling fluid passes through the wellbore, properties of the drilling fluid may change as a result of downhole conditions. For example, the drilling fluid's density may change due to entrainment of gas or "cuttings," pieces of rock from the subsurface formation. By monitoring and analyzing the changes undergone by the drilling fluid as it passes through the wellbore, a drilling operator can gain insight into the effectiveness of the drilling operations and optimize the drilling operations accordingly. Further, analysis of drilling fluids can significantly improve the overall safety of drilling operations by allowing drilling operators to identify problematic conditions before they endanger equipment, personnel, or the environment.

Recent developments in metering technology have significantly improved the ability of drilling operators to collect drilling fluid data during drilling operations. For example, the introduction of Coriolis meters suitable for drilling fluids and sized for the flow requirements of drilling operations have enabled drilling operators to measure flow rate and density of drilling fluids in real time. Given this increased availability of drilling fluid data, new methods and tools for effectively monitoring and analyzing the drilling fluid data are required so that drilling operators can maximize the operational benefits associated with improved metering.

BRIEF DESCRIPTION OF THE DRAWINGS

Embodiments and advantages of the present invention may be best understood by one of ordinary skill in the art by referring to the following description and accompanying drawings. In the drawings.

DETAILED DESCRIPTION

For the purposes of this disclosure, a "fluid" may be, but is not limited to, a gas, a liquid, an emulsion, a slurry, and/or a stream of solid particles that has flow characteristics similar to liquid flow.

"Formation" and "subsurface formation" refer to a body or section of geologic strata, structure, formation or other subsurface solid or collected material that is sufficiently distinctive and continuous with respect to other geologic strata or characteristics that it can be mapped, for example, by seismic techniques. A formation can be a body of geologic strata of predominantly one type or a combination of types, or a fraction of strata having substantially common set of characteristics. A formation can contain one or more hydrocarbon-bearing zones. Note that the terms formation, hydrocarbon bearing subterranean formation, reservoir, and interval may be used interchangeably, but may generally be used to denote progressively smaller subsurface regions, zones, or volumes. More specifically, a geologic formation may generally be the largest subsurface region, a subterranean formation may generally be a region within the geologic formation and may generally be a hydrocarbon-bearing zone (a formation, reservoir, or interval having oil, gas, heavy oil, and any combination thereof), and an interval may generally refer to a sub-region or portion of a reservoir. A hydrocarbon-bearing zone can be separated from other hydrocarbon-bearing zones by zones of lower permeability such as mudstones, shales, or shale-like (highly compacted) sands. In one or more embodiments, a hydrocarbon-bearing zone may include heavy oil in addition to sand, clay, or other porous solids.

"Formation fluids" refer to fluids present in a formation and may include pyrolyzation fluid, synthesis gas, mobilized hydrocarbons, and water (steam). Formation fluids may include hydrocarbon fluids as well as non-hydrocarbon fluids.

The term "wellbore" refers to a hole in a formation made by drilling or insertion of a conduit into the formation. A wellbore may have a substantially circular cross section, or another cross-sectional shape. As used herein, the terms "well" and "opening," when referring to an opening in the formation may be used interchangeably with the term "wellbore."

Illustrative embodiments of the present invention are described in detail herein. In the interest of clarity, not all features of an actual implementation may be described in this specification. It will be appreciated that in the development of any such embodiment, numerous implementation-specific decisions may be made to achieve the specific implementation goals, which may vary from one implementation to another. Moreover, it will be appreciated that such a development effort might be complex and time-consuming, but would nevertheless be a routine undertaking for those of ordinary skill in the art having the benefit of the present disclosure.

In no way should examples of embodiments in this disclosure be read to limit, or define, the scope of the invention. Embodiments of the present disclosure may be applicable to horizontal, vertical, deviated, or otherwise nonlinear wellbores in any type of subterranean formation. Embodiments may be applicable to injection wells as well as production wells, including hydrocarbon wells. Embodiments may be implemented using a tool that is made suitable for testing, retrieval and sampling along sections of the formation. Embodiments may be implemented with tools that, for example, may be conveyed through a flow passage in a tubular string or using a wireline, slickline, coiled tubing, downhole robot or the like. "Measurement-while-drilling" ("MWD") is the term generally used for measuring conditions downhole concerning the movement and location of the drilling assembly while the drilling continues. "Logging-while-drilling" ("LWD") is the term generally used for similar techniques that concentrate more on formation parameter measurement. Devices and methods in accordance with certain embodiments may be used in one or more of wireline, MWD and LWD operations.

The present application is directed to methods and systems for monitoring drilling operations, and specifically for monitoring drilling operations by analysis of drilling fluids.

Figure 1:
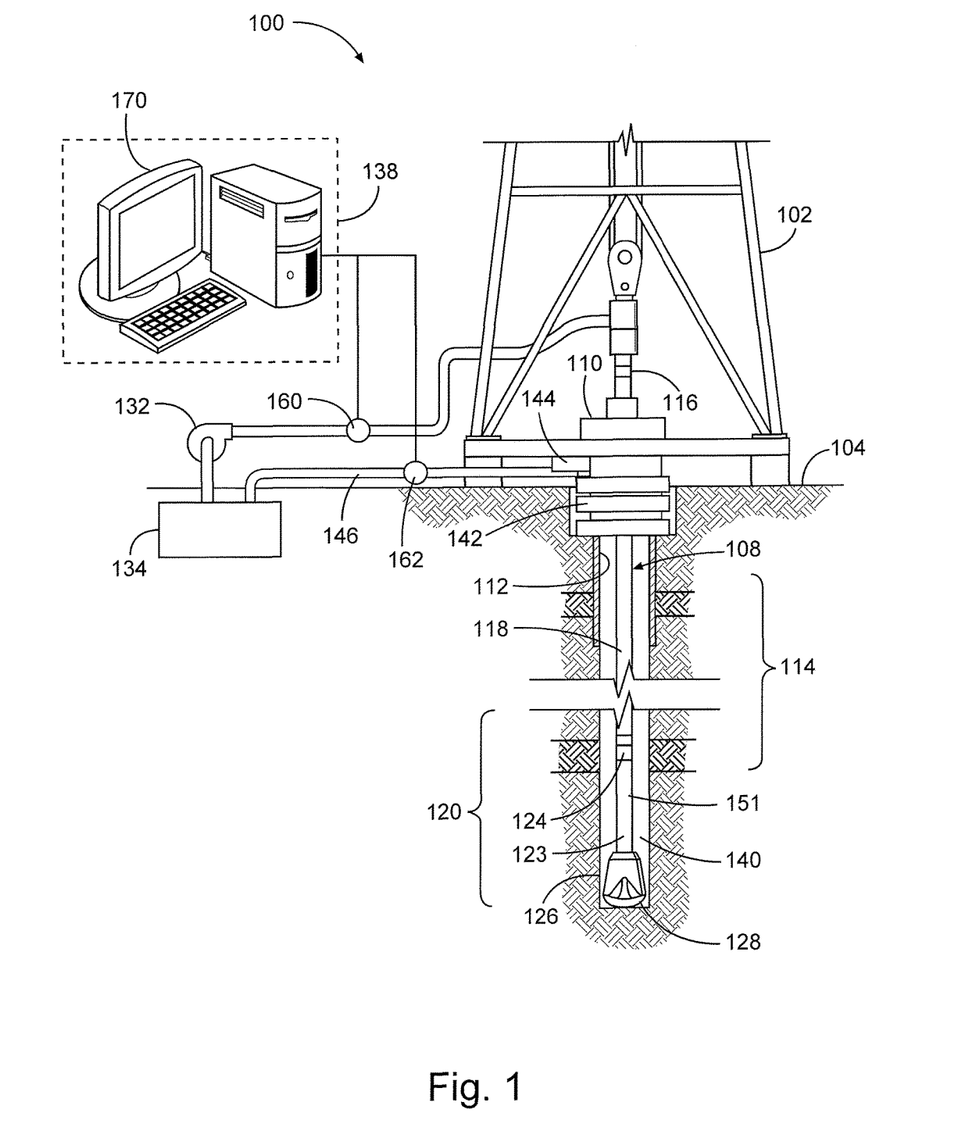
FIG. 1 illustrates a system for drilling operations, according to one embodiment of the invention.

FIG. 1 is a schematic drawing of a drilling system including a system for monitoring drilling fluids according to one embodiment. A drilling system 100 includes a drilling rig 102 located at a surface 104 of a wellbore 112. A hollow drill string 108 is supported by the drill rig 102 and penetrates the surface 104 into a subsurface formation 114 through a rotary table 110. The rotary table 110 rotates the drill string 108. The drill string 108 includes a Kelly 116, a drill pipe 118 and a bottom hole assembly 120 located at the lower portion of the drill pipe 118. The bottom hole assembly 120 may include a drill collar 123, a downhole tool 124 and a drill bit 126. The downhole tool 124 may be any of a number of different types of tools including MWD tools or LWD tools. Any or all of the drilling operations may be performed by a drilling operator or automatically by a control system 138.

In addition to the downhole tool 124, the drill string 108 may include sensors 151 for monitoring and measuring different downhole parameters. These parameters may include temperature and pressure of the wellbore; the resistivity, density, or porosity of the surrounding formation; and the size, shape, and alignment of the borehole 112; or any other property of interest.

During drilling, the drill string 108 is rotated by the rotary table 110. The rotation of the drill string causes the drill bit 126 to remove material from the subsurface formation 114, the removed material forming "cuttings" 128 within the wellbore 112.

As part of drilling operations, a drilling fluid may be circulated through the wellbore 112. In one embodiment, the drilling fluid is pumped by a drilling fluid pump 132 into the drill string 108 from a drilling fluid reservoir 134. The drilling fluid travels through the hollow interior of the drill string 108, through the drill bit 126, and into the wellbore 112. The drilling fluid returns to the surface via an annulus 140 formed by the drill string 108 and the wellbore 112. At the surface, the wellbore 112 may be capped by a blowout preventer 142 having a bell nipple 144. After passing through the bell nipple 144, the drilling fluid may travel through an outlet pipe 146 to a storage or containment pond or to the reservoir 134 for use in later drilling operations. Cuttings and other impurities may be removed from the drilling fluid by filtration or by allowing the cutting or impurities to settle out of the fluid.

Drilling fluid may be circulated through the wellbore to perform various functions, including supporting the drill string 108; cooling and lubricating the drill bit 126; maintaining hydrostatic pressure on the subsurface formation 114 and formation fluids to prevent well blowouts; improving the stability of the wellbore 112; and removing cuttings 128 from the wellbore. The drilling fluid may be formulated to perform one or more functions particularly effectively. For example, "sweep" is a high-density drilling fluid formulated for improved removal of cuttings.

The control system 138 may monitor one or more properties of the drilling fluid as the drilling fluid enters and exits the wellbore 112. The property may be any measurable property of the fluid, including properties that are known to change as the drilling fluid passes through the wellbore. For example, mass, volume, and density are each properties of the drilling fluid that may change as the fluid passes through the wellbore due to, among other things, cuttings becoming entrained in the fluid.

To monitor the fluid properties, the system 100 may include an inlet meter 160 located between the drilling fluid pump 132 and the drill string 108 and an outlet meter 162 located between the wellbore 112 and the reservoir 134. In one embodiment, at least one of the inlet meter 160 and the outlet meter 162 are a type of meter capable of simultaneously measuring two or more of mass flow rate, volumetric flow rate, and density. For example, a Coriolis meter, which may be configured to simultaneously measure mass flow rate and density may be used as the inlet meter 160 and the outlet meter 162. In some embodiments, measurements taken by the inlet meter 160 may be replaced by a calculated value based on speed and size of the drilling fluid pump 132 and tabulated or historical data of drilling fluid properties.

The inlet meter 160 and the outlet meter 162 are installed as close to the wellbore as is practical. Doing so generally lessens any influence on the fluid properties not directly related to passage through the wellbore 112. Equipment present in the system 100 may limit or make certain placements of the inlet meter 160 and the outlet meter 162 more convenient. For example, when a blowout preventer 142 is present, the outlet meter 162 may be easier to install and maintain if installed at the bell nipple 144 instead of in piping downstream of the blowout preventer 142.

The control system 138 may be centralized or distributed and may include one or more computer systems 170. Each computer system may have at least a processor for executing instructions and a memory for storing instructions and other data related to the computer system and the drilling operations. A computer system may be one of a variety of devices having a processor and memory, including: a personal computer (laptop or desktop), a server, a workstation, a microcontroller, a microcomputer, a programmable logic controller (PLC), an integrated circuit, a mobile device such as a smartphone or personal data assistant (PDA), or any similar system. Although many of these devices combine a processor and a memory in a single assembly, the processor and memory may be distributed among several devices capable of communicating with each other.

The memory for storing instructions may be in any format or combination of memory formats known in the art and accessible, directly or indirectly, by the processor. The memory may be in the form of installation memory, such as an installation CD/DVD-ROM or USB "thumb" drive, system memory (i.e., RAM), or other forms of computer storage including mechanical hard drives, solid state hard drives, optical discs, tape drives, flash memory, or SD cards. Depending on the type of memory used, the memory may be configured in a RAID or similar arrangement that provides redundancy or improved performance.

Instructions executed by the processor may be stored in the memory as software, firmware, or any other format suitable for execution by the processor. The programs stored in memory may be created using any programming techniques and in any programming language.

In one embodiment, the control system may perform one or more of a variety of functions including controlling drilling equipment; collecting data from sensors; retrieving data from logs or look-up tables; performing calculations on the collected or retrieved data for analysis; monitoring the drilling operations; communicating data to other computers or control systems via a local network or the internet; and storing data in a database or other similar form of collected data.

A drilling operator may access the control system through a graphical user interface (GUI) as presented to the drilling operator on a display. In one embodiment, the GUI may dynamically display data in real-time. The GUI may also display historical data, enabling an operator to review data collected earlier in the drilling operation or during other drilling operations. The GUI may display graphs, charts, or other forms of data that may be manipulated or customized by the user or a system administrator to emphasize particular data of interest. For example, the user may add trend lines, change colors, or limit the data to a specific period of the drilling operations.

The control system may be configured to issue alarms to personnel and equipment if the control system detects an abnormal condition. For example, the control system may issue an alarm if a sensor reading or a calculation result falls outside of a predetermined range of safe values. In response to the alarm, drilling operators may manually modify drilling operations to avoid potential harm to equipment, personnel, and the environment. Alternatively, the control system or drilling equipment may automatically respond to the alarm by entering into an alternate mode of operation directed to resolving the abnormal condition. If the abnormal condition is not removed after a certain period of time, worsens, or is sufficiently outside of normal operating conditions, the control system may send an emergency shut-down signal, stopping certain pieces of drilling equipment or halting drilling operations altogether.

Figure 2:
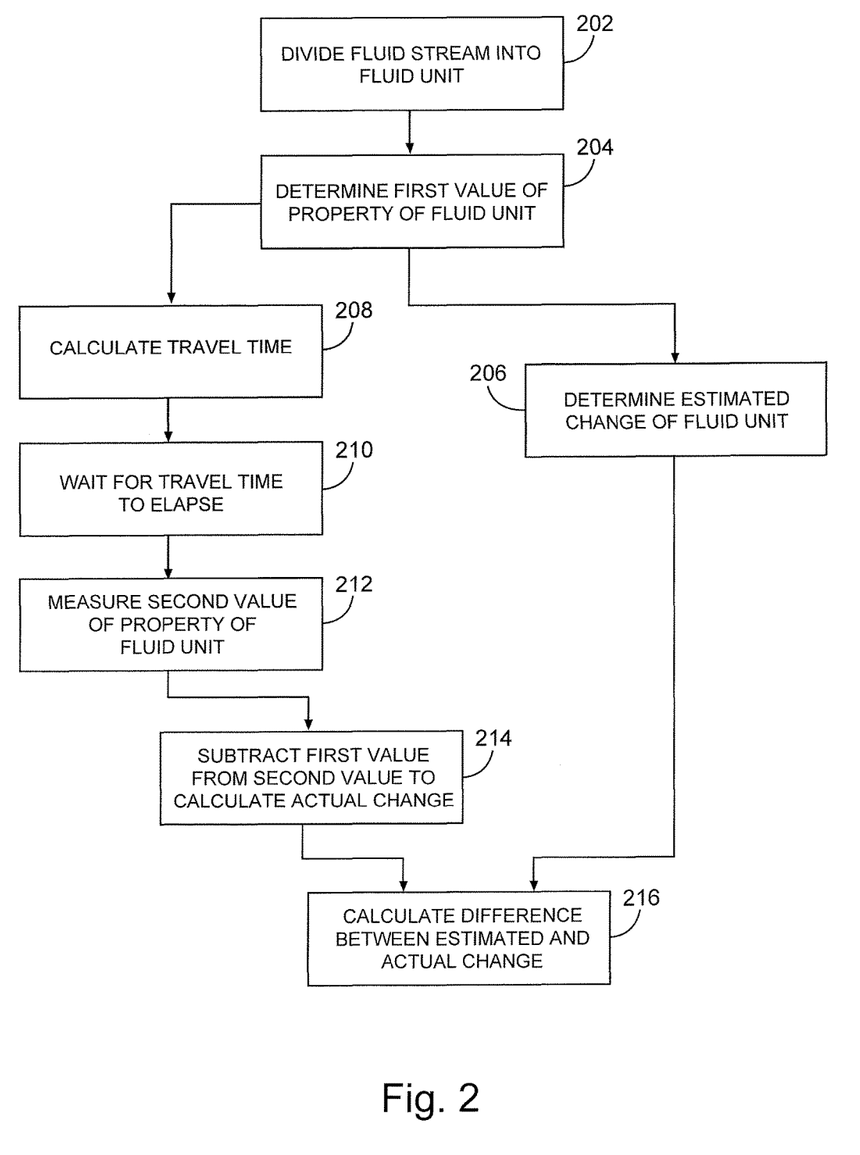
FIG. 2 is a flow chart depicting the process of monitoring fluid units.

FIG. 2 is a flow chart illustrating a method for monitoring changes in a drilling fluid implemented in the control system according to one embodiment. A stream of drilling fluid is divided into at least one discrete fluid unit 202 by the control system. The amount of the drilling fluid in each fluid unit may be based on volume of the fluid unit, mass of the fluid unit, or any other suitable division. If an inlet meter is present, measurements from the inlet meter may be used by the control system to divide the fluid stream. As an alternative to using the inlet meter, the division of the drilling fluid may be based on characteristics and measurements from a drilling fluid pump used to circulate the drilling fluid through the wellbore. For example, the division of the fluid may be based on a predetermined number of pump cycles.

Before a fluid unit enters the wellbore, a first value for a property of the fluid unit is determined 204. The property may be directly measured using an inlet meter or may be calculated based on known parameters such as pump speed, pump volume, and fluid density. After the first value of the property is determined, an estimated change in the property is determined to predict the change in the property of the fluid unit as it passes through the wellbore. The estimated change in the fluid property may be determined by experimental results, analysis of data from previous drilling operations, predictive modelling, or other suitable methods.

After the fluid unit has circulated through the wellbore, a second value of the property is measured 212 by an outlet meter and an actual change of the property is calculated by subtracting the first value of the property from the second value of the property 214. The actual change in the property is then compared to the estimated change in the property 216.

Matching of the first values and second values for a particular fluid unit is performed by calculating a travel time 208 for the fluid unit to pass from a first location where the first value is determined, to a second location, where the second value is measured. Specifically, a first value for a fluid unit is measured at the first location, then, after the travel time has elapsed, a second value for the fluid unit is measured at the second location.

In some embodiments, the travel time is the sum of an inflow time and an outflow time. The inflow time is the time required for a fluid unit to travel between the first location where the first value is measured and the bottom of the wellbore. The outflow time is the time required for the fluid unit to travel from the bottom of the wellbore to the second location where the second value is measured.

Generally, travel time is calculated by determining a total volume between the first and second locations and dividing the volume by the flow rate of the drilling fluid. In embodiments where the travel time is divided into an inflow time and an outflow time, the inflow time is determined based on an inflow volume. The inflow volume is the volume of a flow path from the first location to the bottom of the drill string. The inflow volume is defined by inflow equipment including pipes and hoses between the first location point and the drill string inlet, the drill string, the drill bit, and any volumes of fittings or other equipment between the first location and the drill bit.

After the first value is measured at the first location and the inflow time elapses, the fluid unit is assumed to be exiting the drill string and beginning to travel back to the surface. Similar to the inflow time, the outflow time may be calculated based on an outflow volume. The outflow volume is defined by the annulus between the drill string and the well-bore and any equipment through which the fluid unit may flow as it returns to the surface and to the second point of measurement.

After the outflow time elapses 210, the fluid unit is assumed to have reached the second location and the second value is measured 212. As a result, the first and second values generally correspond to the same fluid unit.

The steps depicted in FIG. 2 may be applied to any number of fluid units.

To facilitate calculating the inflow volume and the outflow volume, a volume or a geometry for one or more pieces of inflow and outflow equipment may be stored in a database or lookup table for retrieval by the control system. In the case of a stored geometry, the control system may calculate a volume corresponding to the geometry using general mathematical principles. Once the control system determines the volume of each piece of inflow or outflow equipment, the volumes of each piece of inflow or outflow equipment may be summed to calculate the inflow or outflow volume, respectively. In addition to stored volume and geometry data, in some embodiments, values used in calculating the inflow or outflow volume may be collected during drilling operations. For example, some values may be determined dynamically by using MWD tools.

Once the inflow or outflow volume is calculated, the inflow or outflow time may be determined by dividing the inflow or outflow volume by the flow rate of the drilling fluid. In the above embodiment, flow rate is assumed to be constant. However, flow rate of the drilling fluid may vary due to changes in the drilling fluid and inconsistencies in pump performance. To accommodate for potential variations in flow rate, one embodiment of the system may periodically sample the flow rate of the drilling fluid and update the travel time accordingly. Further, flow rate throughout sections of the system may be inconsistent due to the presence of certain pieces of drilling equipment. For example, deep sea drilling may require one or more booster pumps to bring drilling fluids to the surface due to the depths involved in deep sea drilling. Accordingly, proper calculation of travel time may need to account for variations in flow rates in different subsections of the inflow and outflow volumes.

In another embodiment, the fluid unit may be tracked as it passes through the wellbore. Tracking involves determining the location of the fluid unit at intermediate points between the first and second location.

In general, if an initial location of a fluid unit and a flow rate of the fluid unit are known, a final location of the fluid unit may be determined as it moves along a flow path having a known cross-sectional area according to the formula:

$$x_{final} = x_{initial} + \Delta t \times Vdot \times A$$

where $x_{final}$ is a final location of the fluid unit along the flow path, $x_{initial}$ is an initial location of the fluid unit along the flow path, $\Delta t$ is the time for the fluid unit to travel between $x_{final}$ and $x_{initial}$, Vdot is the flow rate of the fluid per unit time, and A is the cross-sectional area of the flow path through which the fluid is flowing.

The above equation may be implemented in an iterative, step-wise manner to determine the location of a fluid unit as it moves along the flow path. To do so, the final location determined by the equation over a first time period is used as the initial location of the fluid unit for a subsequent time period. Repeating this process for a total time while updating the cross-sectional area of the flow path and the flow rate as required produces a set of locations of the fluid unit that tracks the location of the fluid unit over the total time.

This principle may be applied in the current system to track a fluid unit as it passes through the wellbore. Because the system knows or can determine an initial position of the fluid unit (the first location where the first value is measured), the geometry of the flow path, and the flow rate of, the system may determine the fluid unit's final position after a period of time has elapsed. The final position of the fluid unit may then be used as a new initial position for a subsequent determination of the fluid unit location. Iterating this process over the entire travel time enables the system to determine a location of the fluid unit corresponding to each time period.

The locations may be calculated in real time by periodically sampling the flow rate and recalculating the inflow and outflow volumes. Based on the needs of the drilling operator, the frequency of the sampling and recalculation may be adjusted to minimize use of computational resources and avoid collecting unnecessary data. As an alternative to real-time tracking, location data may be generated by assuming a constant flow rate and estimating the inflow and outflow geometries.

Tracking the fluid units provides additional detail regarding the drilling operations by allowing correlation of the location of a fluid unit with a change in its properties. For example, tracking may be used to determine the time at which a fluid unit passed through the drill bit. If the fluid unit passed through the drill bit during a time when drilling was not occurring and no cuttings were located at the bottom of the wellbore, an increase in density of the fluid unit might indicate washout or collapse of the wellbore.

The data collected for each fluid unit may be displayed by the control system in real time or logged by the control system in a file or database. Analysis of the fluid unit data by an operator or by the control system may be performed on a single fluid unit or a set of fluid units. A set of fluid units may consist of the entire set of fluid units that have been measured by the system or may be a subset of all fluid units. When analyzing a set of fluid units, data may be numerically integrated for analysis of totalized values. For example, the masses of a set of fluid units may be integrated to determine their the total mass or total change in mass.

Monitoring of the fluid units can enable an operator or control system to analyze the effectiveness of various drilling operations and detect abnormalities during the drilling process. The following example illustrates how the system and method may be used to monitor and analyze drilling operations. Specifically, the following examples illustrate applications of the system to monitor the effectiveness of cuttings removal and to detect the phenomenon of ballooning. These examples are intended only to illustrate, not limit, embodiments of the disclosed system and method. For example, monitoring changes in fluid units in accordance with the disclosed system and method may be used for monitoring fluid losses to the formation, detecting "kicks" caused by sudden influxes of formation fluids into the wellbore, and monitoring "bottoms up" for settling or barite sag when restarting drilling operations after an interruption.

Figure 3:
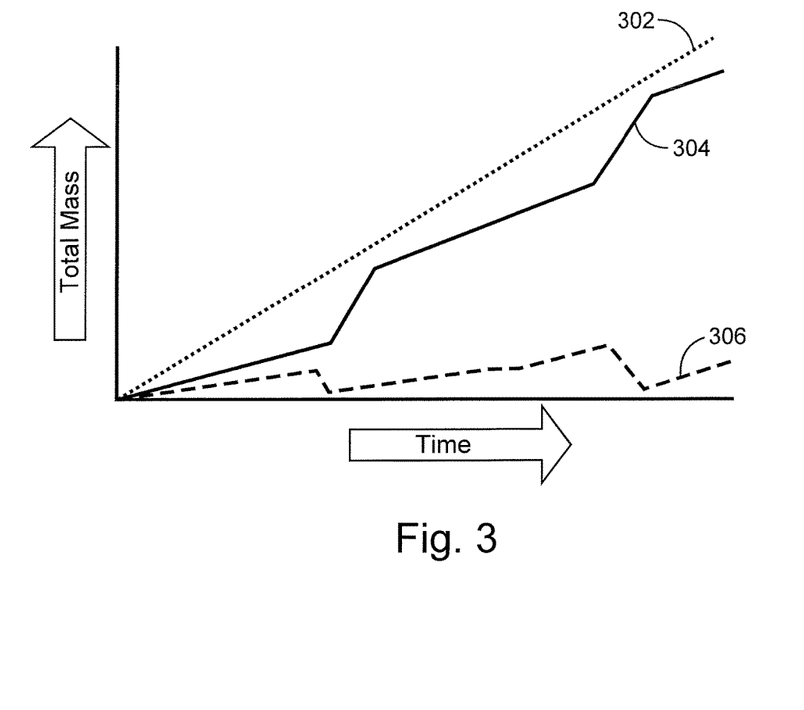
FIG. 3 is a graph depicting one embodiment in which changes in mass over time may be used to determine the effectiveness of cuttings removal.

FIG. 3 depicts a graph as may be presented by the GUI in accordance with one embodiment. The graph depicts total mass of a fluid exiting a wellbore as measured by the system over time. The graph includes three lines: theoretical total mass 302, measured total mass 304, and the difference between the theoretical mass and the measured mass 306. The theoretical total mass is the estimated mass based on the initial mass of the fluid plus any predicted change in the fluid as a result of cuttings becoming entrained in the fluid. The measured mass on the other hand, represents the actual mass of the fluid as it exits the wellbore. As a result, the difference between the theoretical and measured masses indicates that not all cuttings have been swept from the wellbore. Further, the inconsistent slope of the measured mass line indicates that cuttings are not swept from the wellbore in at a consistent rate.

By examining individual fluid units or sets of fluid units, an operator could determine specific causes of the difference in mass or the changing sweep rate. For example, a first series of fluid units with less than expected masses followed by a second series of fluid units having expected masses could indicate a decreased diameter of the wellbore when the first series of fluid units passed through the drill bit. As another example, a first series of fluid units with expected masses followed by a second series of fluid units with higher than expected masses could indicate an increased diameter of the wellbore or partial collapse of the wellbore, either of which would introduce additional cuttings into the wellbore.

Figure 4:
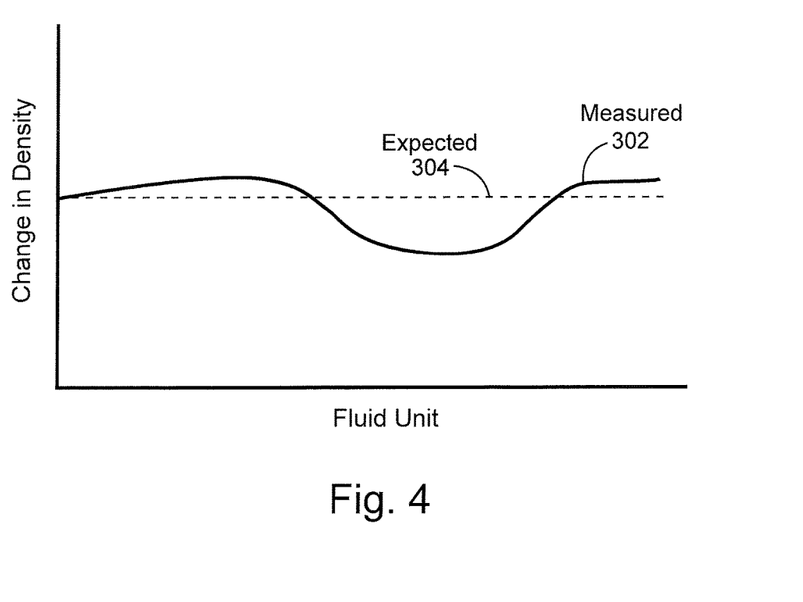
FIG. 4 is a second graph depicting another embodiment in which changes in density of a series of fluid units may be used to detect ballooning.

FIG. 4 depicts a second graph as may be presented by the GUI. FIG. 4 depicts an expected change in density 402 and a measured change in density 404 of a series of fluid units. Notably, the density measurements are depicted as being associated with specific fluid units and are independent of time. By associating measurements with fluid units instead of time, an operator can account for interruptions or delays in drilling operations that may impact measurements.

FIG. 4 also illustrates how the system may detect ballooning. Similar to a balloon that is inflated and then releases air when inflation stops, ballooning occurs when pumped fluids are taken in by the formation and then returned to the wellbore once pumping stops. As depicted in FIG. 4, when fluids are returned to the wellbore, fluid units may become diluted as indicated by a decrease in density.

The invention claimed is:

1. A method of monitoring drilling operations comprising:
passing a flow of a drilling fluid through a wellbore;
prior to the flow of the drilling fluid entering the wellbore, dividing the flow of the drilling fluid into a plurality of discrete drilling fluid units;
for each of the plurality of discrete drilling fluid units:
determining a first value of a property of a discrete drilling fluid unit of the plurality of discrete drilling fluid units at a first location at a surface before the discrete drilling fluid unit passes through the wellbore, wherein the property comprises at least one of a mass, a volume, and a density;
determining an estimated change in the property of the discrete drilling fluid unit to predict a change in the property of the discrete drilling fluid unit as the discrete drilling fluid unit passes through the wellbore;
measuring a second value of the property of the discrete drilling fluid unit at a second location at the surface downstream from the first location as the discrete drilling fluid unit passes the second location upon exiting the wellbore;
calculating an actual change in the property of the discrete drilling fluid unit by comparing the first value and the second value; and
comparing the actual change in the property of the discrete drilling fluid unit to the estimated change in the property of the discrete drilling fluid unit, wherein comparison of the actual change to the estimated change are not made between different discrete drilling fluid units of the plurality of discrete drilling fluid units;
modifying a drilling operation based on the comparison to an alternate mode of operation.

2. The method of claim 1, further comprising
calculating a travel time for each of the plurality of discrete drilling fluid units between the first and the second location, wherein the second value is measured at the second location after the travel time has elapsed from when the first value is measured at the first location.

3. The method of claim 1 further comprising
recording and storing the data in a memory for at least one of the first value, the estimated change, the second value, and the actual change.

4. The method of claim 1 further comprising
determining a difference between the actual change and the estimated change and generating a signal selected from the group of an alarm signal and a shutdown signal if the difference exceeds a predetermined threshold.

5. The method of claim 1 further comprising the step of
for each of the plurality of discrete drilling fluid units
tracking the discrete drilling fluid unit as it moves through the wellbore, the tracking step comprising the steps of
determining a flow path geometry having a total volume between the first location and the second location,
measuring a volume flow rate of the flow of the drilling fluid,
calculating a travel time by dividing the total volume by the volume flow rate, and
determining, based on the travel time and the flow path geometry, at least one location of the discrete drilling fluid unit as the discrete drilling fluid unit passes between the first location and the second location.

6. The method of claim 1 wherein
for each of the plurality of discrete drilling fluid units, the first value of the property of the discrete fluid drilling unit is determined by directly measuring the property of the discrete drilling fluid unit.

7. The method of claim 1 wherein
for each of the plurality of discrete drilling fluid units, the first value of the property of the discrete drilling fluid unit is determined indirectly by measuring a system property and deriving the first value from the system property, wherein the system property is a property of the drilling fluid or a downhole parameter of the wellbore.

8. The method of claim 1 wherein
for each of the plurality of drilling discrete drilling fluid units, the estimated change in the property of the discrete drilling fluid unit is based on wellbore cuttings being introduced into the discrete drilling fluid unit.

9. The method of claim 1 wherein
for each of the plurality of discrete drilling fluid units, the property of the discrete drilling fluid unit is selected from the group consisting of mass, volume, and density.

10. A system for monitoring drilling operations comprising:
a drilling fluid flow path comprising
a first location at the surface,
a second location at the surface and downstream from the first location,
a volume disposed between the first location and the second location, the volume being defined in part by a wellbore and a drill string,
a pump for circulating a drilling fluid from the first location to the second location through the volume;
a meter for determining a first value of a property of any of a plurality of discrete drilling fluid units of the drilling fluid at the first location, wherein the property comprises at least one of a mass, a volume, and a density;
a meter for measuring a second value of the property of the discrete drilling fluid unit of the plurality of discrete drilling fluid units at the second location; and
a control system, wherein the control system
estimates a change in the property of the discrete drilling fluid unit of the plurality of discrete drilling fluid units as the discrete drilling fluid unit moves from the first location to the second location,
determines an actual change in the property by comparing the first value and the second value of the discrete drilling fluid unit of the discrete drilling fluid units, and
compares the estimated change in the property to the actual change in the property of the discrete drilling fluid unit, wherein comparisons of the estimated change to the actual change are not made between different discrete drilling fluid units of the plurality of discrete drilling fluid units.

11. The system of claim 10 wherein
the meter for determining the first value of the property of the discrete drilling fluid unit directly measures the property of the discrete drilling fluid unit.

12. The system of claim 11 wherein
the meter for determining the first value is a meter capable of simultaneously measuring volume and mass.

13. The system of claim 12 wherein the meter for determining the first value is a Coriolis meter.

14. The system of claim 10 wherein the meter for determining the first value of the property of the discrete drilling fluid unit determines the first value indirectly by deriving the first value from a property of the system other than the property of the discrete fluid.

15. The system of claim 10 wherein the meter for determining the first value is selected from the group of a meter for directly measuring the property of the drilling fluid at the first location and a meter measuring pump performance from which the property of the drilling fluid at the first location may be calculated.

16. The system of claim 10 wherein the meter for determining the second value is a meter capable of simultaneously measuring volume and mass.

17. The system of claim 10 wherein the meter for determining the second value is a Coriolis meter.

18. The system of claim 10 wherein the control system records and stores the data in a memory for at least one of the first value, the estimated change, the second value, and the actual change.

19. The system of claim 10 wherein the control system generates a signal selected from the group of an alarm signal and a shutdown signal if the actual change and the estimated change differ by a predetermined amount.

* * * * *